United States Patent [19]

Baumann et al.

[11] Patent Number: 4,639,531

[45] Date of Patent: Jan. 27, 1987

[54] PROCESS FOR THE PREPARATION OF DIMETHYLMALEIC ANHYDRIDE

[75] Inventors: Marcus Baumann; Werner Breitenstein, both of Basel, Switzerland

[73] Assignee: Ciba-Geigy Corporation, Ardsley, N.Y.

[21] Appl. No.: 762,752

[22] Filed: Aug. 6, 1985

[30] Foreign Application Priority Data

Aug. 15, 1984 [CH] Switzerland .......................... 3910/84

[51] Int. Cl.$^4$ .......................................... C07D 307/60
[52] U.S. Cl. .................................................... 549/261
[58] Field of Search .......................................... 549/261

[56] References Cited

U.S. PATENT DOCUMENTS 3,818,050 6/1974 Baumann et al. .................. 549/261
3,833,619 9/1974 Baumann et al. .................. 549/261
4,480,106 10/1984 Breitenstein et al. .............. 549/253

FOREIGN PATENT DOCUMENTS 870681 6/1961 United Kingdom .

OTHER PUBLICATIONS

M. E. Baumann et al, Helv. Chim Acta, 61, 2751 (1978).

*Primary Examiner*—Henry R. Jiles
*Assistant Examiner*—Bernard I. Dentz
*Attorney, Agent, or Firm*—Luther A. R. Hall

[57] ABSTRACT

The reaction of maleic acid, fumaric acid and/or maleic anhydride at elevated temperature and in the presence of catalytic amounts of a heterocyclic amidine or a salt thereof with protonic acids affords dimethylmaleic anhydride in good yield.

11 Claims, No Drawings

PROCESS FOR THE PREPARATION OF DIMETHYLMALEIC ANHYDRIDE

The present invention relates to a process for the preparation of dimethylmaleic anhydride from maleic acid, fumaric acid and/or maleic anhydride at elevated temperature and in the presence of catalytic amounts of a heterocyclic amidine or amidine salt.

It is known from German published applications Nos. 2 233 862 and 2 233 889 that dimethylmaleic anhydride is formed by reacting 2 mol of maleic acid, fumaric acid and/or maleic anhydride with 1 mol of a heterocyclic amidine or amidine salt at elevated temperature and by subsequent acid hydrolysis. It has now been found that the use of catalytic amounts of an amidine or amidine salt in this reaction is sufficient to obtain the desired dimethylmaleic anhydride in high yield without having to carry out acid hydrolysis.

Accordingly, the present invention relates to a process for the preparation of dimethylmaleic anhydride by reacting 2 equivalents of maleic acid, fumaric acid and/or maleic anhydride at a temperature of at least 90° C. and in the presence of an amidine of formula I and/or an amidine salt of formula II

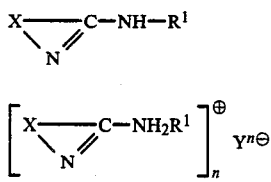

in which formulae $R^1$ is a hydrogen atom, alkyl, cycloalkyl, carboxyalkyl, aryl, aralkyl, alkaryl, or alkaralkyl, Y is the anion of an inorganic or organic protonic acid, n is an integer from 1 to 3, and X, together with the group

forms the radical of a substituted or unsubstituted 5- or 6-membered heterocyclic ring which may contain further hetero atoms, which process comprises employing the compounds of formulae I and II in catalytic amounts of 0.1 to 15 mol%, based on maleic acid, fumaric acid and/or maleic anhydride.

In the process of the present invention, it is preferred to employ maleic acid, maleic anhydride or 1:1 mixtures (molar ratio) thereof.

Radicals of an unsubstituted or further substituted 5- or 6-membered heterocyclic ring which may contain further hetero atoms, which radicals are formed by X together with the group

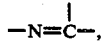

are e.g. imidazolyl, pyrazolyl, triazolyl, thiazolyl, isothiazolyl, oxadiazolyl, thiadiazolyl, oxazolyl, pyridinyl, pyridazinyl, pyrimidinyl, pyrazinyl and triazinyl radicals.

If these radicals are further substituted, they may contain for example halogens such as fluorine, chlorine or bromine, phenyl groups, alkyl or alkoxy groups having 1 to 4 carbon atoms, amino groups, monoalkylamino or dialkylamino groups having 1 to 4 carbon atoms in each alkyl moiety, or hydroxyl groups, or they may be condensed with further homocyclic or heterocyclic rings. Preferred substituents are halogen, $C_1$-$C_4$-alkyl and $C_1$-$C_4$alkoxy. Examples of condensed 5- or 6-membered heterocyclic ring systems are: benzimidazole, benzothiazole, benzoxazole, pterin, purine, quinoline, isoquinoline, naphthyridine, phthalazine, cinnoline, quinazoline and quinoxaline.

Radicals or a 5- of 6-membered heterocyclic ring which are formed by X together with the group

are preferably not further substituted. The heterocyclic ring is preferably a 2-thiazolyl radical, especially the 2-pyridinyl radical.

The amidines of formula I are known or may be prepared in a manner known per se. Examples of suitable compounds of formula I are: 2-aminoimidazole, 2-aminobenzimidazole, 3-aminopyrazole, 3-amino-5-methylpyrazole, 3-amino-4-bromo-5-methylpyrazole, 3-amino-1-phenylpyrazole, 3-amino-1,2,4-triazole, 3,5-diamino-1,2,4-triazole, 4-amino-1,2,3-triazole, 2-amino-1,3-thiazole, 3-aminoisothiazole, 2-amino-5-chlorethiazole, 2-amino-4-phenylthiazole, 2-aminobenzothiazole, 2-amino-6-bromobenzothiazole, 2-amino-4,6-dibromobenzothiazole, 3-amino-4-phenylfurazan, 3-amino-4-methylfurazan, 3-aminoisoxazole, 2-aminooxazole, 2-aminobezoxazole, 2-aminopyridine, 2-amino-3-methylpyridine, 2-amino-4-methylpyridine, 2-amino-6-methylpyridine, 2-amino-5-bromopyridine, 2-amino-6-bromopyridine, 2-amino-5-chloropyridine, 2-amino-3,5-dibromopyridine, 2-amino-3,5-dichloropyridine, 2-amino-3-methylaminopyridine, 2,6-diaminopyridine, 2,3-diaminopyridine, 2-aminopyrazine, 2-aminopyrimidine, 6-amino-2-chloropyrimidine, 6-amino-2,4-dimethypyrimidine, 2-amino-5-bromo-4,6-dimethylpyrimidine, 2-amino-6-chloropyrimidine, 2-amino-4,6-dichloropyrimidine, 6-amino-2,4-dichloropyrimidine, 2-amino-4,6-dimethylpyrimidine, 4,6-diaminopyrimidine, 6-amino-4-methylpyrimidine, 3-aminopyridazine, 2-amino-1,3,5-triazine, 2,4,6-triamino-1,3,5-triazine, 2-amino-4,6-dichloro-1,3,5-triazine, 2-amino-4,6-dimethyl-1,3,5-triazine, 4-amino-6-hydroxy-2-methyl-1,3,5-triazine, 2,4-diamino-6-methyl-1,3,5-triazine, 8-aminopurine, 2-aminopurine, 6-aminopurine(adenine), 2-amino-6-bromopurine, 2-amino-6-chloropurine, 6-amino-2,8-dichloropurine, 8-amino-2,6-dichloropurine, 6-amino-2-methylpurine, 2,8-diaminopurine, 6,8-diaminopurine, 7-methyl-2,6,8-triaminopourine, 1-aminoisoquinoline, 2-aminoquinoline, 2,4-diaminoquinoline, 2-amino-1,7-napthyridine, 2-amino-1,5-naphthyidine, 2-amino-6,7-dimethyl-1,8-naphthyridine, 2-aminoquinoxaline, 2,3-diaminoquinoxaline, 4-aminoquinazoline.

If amidine salts of formula II are employed in the process of the present invention, then n is an integer from 1 to 3 and Y is preferably the anion of formic acid, acetic acid, propionic acid, hydrochloric acid, hydrobormic acid, sulfuric acid or phosphoric acid. However, Y is most preferably the anion of a carboxylic acid having 2 to 4 carbon atoms, in particular acetic acid (n=1). These salts can be prepared in conventional manner by treating the amidine of formula I with the corresponding acid. This preparation can be effected direct in situ or the isolated salt can be used for the reaction.

$R^1$ as alkyl may be linear or branched and preferably contains 1 to 12, most preferably 1 to 6, carbon atoms, e.g. methyl, ethyl, n-propyl, isopropyl, n-butyl, isobutyl, tert-butyl, pentyl, hexyl, octyl, decyl and undecyl. $R^1$ is cycloalkyl preferably contains 5 to 7 ring carbon atoms, e.g. cyclopentyl and cyclohexyl. $R_1$ as carboxyalkyl preferably contains 2 to 12, most preferably 2 to 6, carbon atoms, e.g. carboxymethyl, carboxyethyl, carboxypropyl, carboxybutyl, carboxypentyl, carboxyheptyl, carboxyundecyl.

$R^1$ as aryl preferably contains 6 to 12 carbon atoms, as aralkyl and alkaryl 7 to 16 carbon atoms and as alkaralkyl 8 to 16 carbon atoms. The radicals may be substituted, e.g. by halogen, in particular chlorine, carboxy, $C_1$-$C_4$alkoxy, $NO_2$ or —OH. Examples of such radicals are: phenyl, benzyl, methylphenyl, methylbenzyl and phenylethyl.

In a preferred embodiment, $R^1$ is $C_1$-$C_4$alkyl or phenyl which is unsubstituted or substituted by a chlorine atom, a nitro or a $C_1$-$C_4$alkoxy group, in particular a methoxy group. In accordance with a further preference, $R_1$ is a hydrogen atom.

The reaction temperature is preferably in the range from 110° to 160° C. If desired, the reaction may be carried out under pressure. The compounds of formulae I and II are preferably employed in an amount of 1 to 10 mol%.

The reaction of the present invention may be carried out in an organic solvent which is inert to the reactants. Examples of such solvents are unsubstituted or chlorinated aromatic hydrocarbons, e.g. benzene, toluene, xylenes, chlorobenzene, or dichlorobenzenes, dialkyl sulfoxides, e.g. dimethyl sulfoxide, methyl cellosolve, hexamethylphosphoric triamide, N,N-dialkylamides of a lower monocarboxylic acid, e.g. dimethylformamide or dimethylacetamide, or lower dialkyl esters of carbonic acid, e.g. dimethyl carbonate or diethyl carbonate. Mixtures of such solvents may also be employed. If the amidine salt of the general formula II is prepared direct in situ, the acid used, e.g. an aliphatic $C_2$-$C_4$carboxylic acid, in particular acetic acid, may also be employed as solvent.

In accordance with a preferred embodiment, the reaction of the invention is carried out without addition of a solvent or, in particular, in anhydrous acetic acid. A buffer compound, e.g. an alkali metal acetate such as sodium acetate, may also be added to the reaction mixture. If maleic anhydride is employed alone, it is convenient to add water, advantageously in an amount of 0.5 to 20% by weight, based on the amount of maleic anhydride employed.

The isolation and purification of the reaction product are effected by conventional methods, e.g. distillation, steam distillation, extraction or crystallisation. It is a particular advantage of the process of the present invention that the reaction product can be isolated direct without having to effect acid hydrolysis so that high yields can be obtained. In this process, the amidine compounds can be recovered in quantitative yield.

Dimethylmaleic anhydride is a valuable intermediate for the preparation of light-sensitive polymers containing dimethylmaleic imidyl groups (q.v. German published application No. 2 626 769).

The invention is illustrated in more detail by the following Examples.

EXAMPLE 1

58.0 g (0.5 mol) of maleic acid and 0.85 g (5 mmol) of 2 phenylaminopyridine are boiled under reflux for 48 hours in 200 ml of glacial acetic acid. The glacial acetic acid is subsequently distilled off and the residue is steam distilled. The distillate is filtered and the filtrate is dried, affording 13.2 g (42%) of dimethylmaleic anhydride with a melting point of 91°-93° C. By extracting the mother liquor with ether, a further 3.2 g (10%) of dimethylmaleic anhydride are isolated.

EXAMPLES 2-11

Examples 2 to 11 are carried out under the reaction conditions of Example 1 using the catalysts indicated in the Table.

Examples 2-11

| Example | Catalyst | mol % | yield |
|---------|----------|-------|-------|
| 2 | pyridin-2-yl-NH-CH2-phenyl | 10 | 35.6% |
| 3 | pyridin-2-yl-NH-CH2-CH2-COOH | 10 | 35.6% |
| 4 | benzothiazol-2-yl-NHCH3 | 10 | 33.3% |
| 5 | thiazol-2-yl-NH-phenyl | 10 | 49.5% |
| 6 | pyridin-2-yl-NH-C(CH3)3 | 10 | 68.6% |
| 7 | (methyl)pyridin-2-yl-NH-CH3 | 10 | 55.9% |
| 8 | pyridin-2-yl-NH-CH3 | 10 | 54.1% |
| 9 | pyridin-2-yl-NH-(4-chlorophenyl) | 10 | 57.8% |
| 10 | pyridin-2-yl-NH-(4-nitrophenyl) | 1 | 53% |

-continued

Examples 2-11

| Example | Catalyst | mol % | yield |
|---|---|---|---|
| 11 | 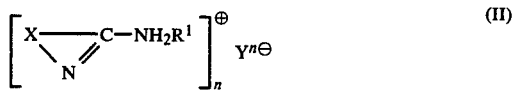 | 10 | 57.8% |

EXAMPLE 12

58.0 g (0.5 mol) of maleic acid are added in portions over 7 hours to a boiling solution of 0.85 g (5 mmol) of 2-phenylaminopyridine in 200 ml of glacial acetic acid. The mixture is subsequently boiled under reflux for 14 hours. Working up as in Example 1 affords 11.2 g (35.6%) of dimethylmaleic anhydride with a melting point of 91°-93° C.

EXAMPLE 13

98.0 g (1 mol) of maleic anhydride, dissolved in 250 ml of glacial acetic acid, and 9 ml of water are added dropwise over 1 hour simultaneously from two drip funnels to a boiling solution of 1.7 g (0.01 mol) of 2-phenylaminopyridine in 50 ml of glacial acetic acid. The mixture is subsequently boiled under reflux for 20 hours. Working up as in Example 1 affords 28.9 g (45.9%) of dimethylmaleic anhydride with a melting point of 91°-93° C.

EXAMPLE 14

A solution of 49.0 g (0.5 mol) of maleic anhydride and 58.0 g (0.5 mol) of maleic acid in 350 ml of glacial acetic acid is added dropwise over 3 hours to a boiling solution of 1.7 g (0.01 mol) of 2-phenylaminopyridine in 50 ml of glacial acetic acid. The mixture is subsequently boiled under reflux for 3 hours. Working up as in Example 1 affords 34.3 g (54.0%) of diemthylmaleic anhydride with a melting point of 91°-93° C.

EXAMPLE 15

A solution of 98.0 g (1 mol) of maleic anhydride in 200 ml of glacial acetic acid is added dropwise over 1 hour to a boiling mixture of 1.7 g (0.01 mol) of 2-phenylaminopyridine and 22.8 g of sodium acetate trihydrate in 100 ml of glacial acetic acid. The mixture is subsequently boiled under reflux for 18 hours. Working up as in Example 1 affords 27.9 g (44.3%) of dimethylmaleic anhydride with a melting point of 91°-93° C.

EXAMPLE 16

58.0 g (0.5 mol) of maleic anhydride and 4.7 g (0.05 mol) of 2-aminopyridine are boiled under reflux for 48 hours in 200 ml of glacial acetic acid. Working up as in Example 1 affords 17.0 g (54%) of dimethylmaleic anhydride with a melting point of 91°-93° C.

What is claimed is:
1. A process for the preparation of dimethylmaleic anhydride by reacting 2 equivalents of maleic acid, fumaric acid and/or maleic anhydride at a temperature of at least 90° C. and in the presence of an amidine of formula I and/or an amidine salt of formula II

$$X\diagdown_{N}\diagup C-NH-R^1 \qquad (I)$$

$$\left[ X\diagdown_{N}\diagup C-NH_2R^1 \right]_n^{\oplus} Y^{n\ominus} \qquad (II)$$

in which formulae $R^1$ is a hydrogen atom, alkyl, cycloalkyl, carboxyalkyl, aryl, aralkyl, alkaryl, or alkaralkyl, Y is an anion of an inorganic or organic protonic acid, n is an integer from 1 to 3, and X, together with the group $$-N=C<,$$

forms the radical of a substituted or unsubstituted 5- or 6-membered heterocyclic ring which may contain further hetero atoms, which process comprises employing the compounds of formulae I and II in catalytic amounts of 0.1 to 15 mol%, based on maleic acid, fumaric acid and/or maleic anhydride.

2. A process according to claim 1, wherein the compounds of formulae I and II are employed in an amount of 1 to 10 mol%.

3. A process according to claim 1, which is carried out in the presence of an inert solvent.

4. A process according to claim 3, wherein the solvent is an aliphatic carboxylic acid having 2 to 4 carbon atoms.

5. A process according to claim 4 wherein the solvent is acetic acid.

6. A process according to claim 1, which is carried out in the temperature range from 110° to 160° C.

7. A process according to claim 1, wherein 0.5 to 20% by weight of water, based on the amount of maleic anhydride, is added if said maleic anhydride is employed alone.

8. A process according to claim 1, which comprises the use of maleic acid, maleic anhydride or a 1:1 mixture (molar ratio) thereof.

9. A process according to claim 1, wherein the heterocyclic ring is a 2-pyridinyl radical or a 2-thiazolyl radical.

10. A process according to claim 8, wherein $R^1$ as a radical other than hydrogen is $C_1$-$C_{12}$alkyl, $C_5$-$C_7$cycloalkyl, $C_2$-$C_{12}$carboxyalkyl, $C_6$-$C_{12}$aryl, $C_7$-$C_{16}$aralkyl, $C_7$-$C_{16}$alkaryl or $C_8$-$C_{16}$alkaralkyl.

11. A process according to claim 8, wherein $R^1$ is a hydrogen atom.

* * * * *